United States Patent
Egorov et al.

(10) Patent No.: US 9,127,023 B2
(45) Date of Patent: Sep. 8, 2015

(54) ELECTROLYTE ADDITIVE AND ELECTROLYTE INCLUDING SAME AND RECHARGEABLE LITHIUM BATTERY INCLUDING ELECTROLYTE

(75) Inventors: Vladimir Egorov, Yongin-si (KR); Woo-Cheol Shin, Yongin-si (KR); Denis Chernyshov, Yongin-si (KR); Makhmut Khasanov, Yongin-si (KR); Pavel Shatunov, Yongin-si (KR); Alexey Tereshchenko, Yongin-si (KR)

(73) Assignee: Samsung SDI Co., Ltd., Giheung-gu, Yongin-si, Gyeonggi-do (KR)

( * ) Notice: Subject to any disclaimer, the term of this patent is extended or adjusted under 35 U.S.C. 154(b) by 455 days.

(21) Appl. No.: 13/604,241

(22) Filed: Sep. 5, 2012

(65) Prior Publication Data

US 2013/0236776 A1    Sep. 12, 2013

(30) Foreign Application Priority Data

Mar. 8, 2012 (KR) .................. 10-2012-0024101

(51) Int. Cl.
*H01M 10/056* (2010.01)
*C07F 5/04* (2006.01)
(Continued)

(52) U.S. Cl.
CPC ............... *C07F 5/04* (2013.01); *H01M 10/052* (2013.01); *H01M 10/0567* (2013.01); *Y02E 60/122* (2013.01)

(58) Field of Classification Search
CPC ... C07F 5/04; H01M 10/052; H01M 10/0567; Y02E 60/122
See application file for complete search history.

(56) References Cited

U.S. PATENT DOCUMENTS 5,534,370 A    7/1996   Kita et al.
6,924,066 B2   8/2005   Heider et al.
(Continued)

FOREIGN PATENT DOCUMENTS

JP    07065843          3/1995
JP    2004095445 A  *   3/2004   ............ H01M 10/40
JP    2007257875 A  *   10/2007

OTHER PUBLICATIONS

Larush-Asraf et al., On the electrochemical and thermal behavior of lithium bis(oxalato)borate (LiBOB) solutions, J Power Sources (2007) 174, pp. 400-407.

(Continued)

*Primary Examiner* — Carlos Barcena
(74) *Attorney, Agent, or Firm* — Robert E. Bushnell, Esq.

(57) ABSTRACT

Disclosed are an electrolyte additive represented by the following Chemical Formula, an electrolyte including the same, and a rechargeable lithium battery. The electrolyte may have high dissolution capability in a non-aqueous organic solvent and high affinity for the surface of a negative electrode while promoting formation of a passivation film on the surface of a positive electrode and/or a negative electrode.

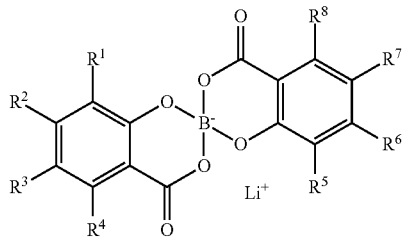

9 Claims, 4 Drawing Sheets

(51) Int. Cl.
*H01M 10/052* (2010.01)
*H01M 10/0567* (2010.01)

(56) References Cited

U.S. PATENT DOCUMENTS

| 7,740,986 | B2 | 6/2010 | Yumoto et al. |
| 2007/0065727 | A1 | 3/2007 | Koike et al. |
| 2010/0040954 | A1 | 2/2010 | Amine et al. |

OTHER PUBLICATIONS

Schmidt et al., Lithium fluoroalkylphosphates: a new class of conducting salts for electrolytes for high energy lithium-ion batteries, J Power Sources (2001) 97-98, pp. 557-560.

Zhang et al., LiBOB-based gel electrolyte Li-ion battery for high temperature operation, J Power Sources (2006) 154, pp. 276-280.

Yang et al., Inorganic additives for passivation of high voltage cathode materials, J Power Sources (2011) 196, pp. 2251-2254.

Xu et al., Formation of the Graphite/Electrolyte Interface by Lithium Bis(oxalato)borate, Electrochem Solid St (2003) 6, 6, pp. A117-A120.

Shieh et al., Effect of mixed LiBOB and LiPF6 salts on electrochemical and thermal properties in LiMn2O4 batteries, J Power Sources (2007) 174, pp. 663-667.

Sasaki et al., Application of Lithium Organoborate with Salicylic Ligand to Lithium Battery Electrolyte, J Electrochem Soc (2001) 148, 9, pp. A999-A1003.

* cited by examiner

ELECTROLYTE ADDITIVE AND ELECTROLYTE INCLUDING SAME AND RECHARGEABLE LITHIUM BATTERY INCLUDING ELECTROLYTE

CLAIM OF PRIORITY

This application makes reference to, incorporates the same herein, and claims all benefits accruing under 35 U.S.C. §119 from an application for ELECTROLYTE ADDITIVE AND ELECTROLYTE INCLUDING SAME AND RECHARGEABLE LITHIUM BATTERY INCLUDING ELECTROLYTE earlier filed in the Korean Intellectual Property Office on 8 Mar. 2012 and there duly assigned Serial No. 10-2012-0024101.

BACKGROUND OF THE INVENTION

1. Field of the Invention

The present invention relates to an electrolyte additive, an electrolyte including the same, and a rechargeable lithium battery.

2. Description of the Related Art

Batteries transform chemical energy generated from an electrochemical redox reaction of a chemical material in the battery into electrical energy. Such batteries are divided into a primary battery, which should be disposed of after the energy of the battery is consumed, and a rechargeable battery, which can be recharged many times. The rechargeable battery can be charged/discharged many times based on the reversible transformation between chemical energy and electrical energy.

Recent developments in high-tech electronics have allowed electronic devices to become small and light in weight, which has lead to an increase in portable electronic devices. As a power source for such portable electronic devices, the demands for batteries with high energy density are increasing and research on lithium rechargeable batteries is in progress.

A rechargeable lithium battery is fabricated by injecting electrolyte into a battery cell which includes a positive electrode including a positive active material capable of intercalating/deintercalating lithium and a negative electrode including a negative active material capable of intercalating/deintercalating lithium.

A conventional electrolyte includes an organic solvent in which a lithium salt is dissolved and which critically influences stability and performance of a rechargeable lithium battery.

SUMMARY OF THE INVENTION

One embodiment provides an electrolyte additive having improved stability and performance.

Another embodiment provides an electrolyte including the electrolyte additive.

Yet another embodiment provides a rechargeable lithium battery including the electrolyte.

According to one embodiment, an electrolyte additive represented by the following Chemical Formula 1 is provided.

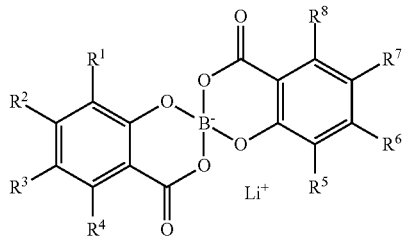

Chemical Formula 1

In Chemical Formula 1, $R^1$ to $R^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitro group, or a combination thereof, and at least one of $R^1$ to $R^8$ may be a substituted or unsubstituted aryl group, a substituted or unsubstituted halogenated aryl group, or a combination thereof.

In the above Chemical Formula 1, at least one of $R^1$ to $R^8$ may be a fluoroaryl group.

In the above Chemical Formula 1, at least one of $R^1$ to $R^8$ may be 2,4-$F_2C_6H_3$.

The electrolyte additive represented by Chemical Formula 1 may include an electrolyte additive represented by the following Chemical Formula 1(a).

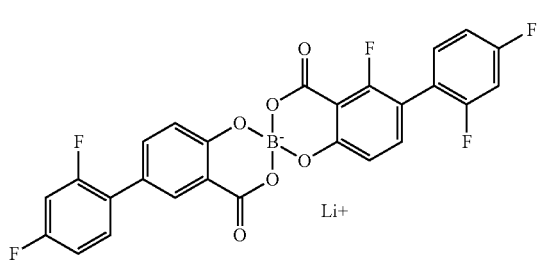

Chemical Formula 1(a)

According to another embodiment, an electrolyte for a rechargeable lithium battery including an additive represented by the following Chemical Formula 1, a non-aqueous organic solvent, and a lithium salt is provided.

Chemical Formula 1

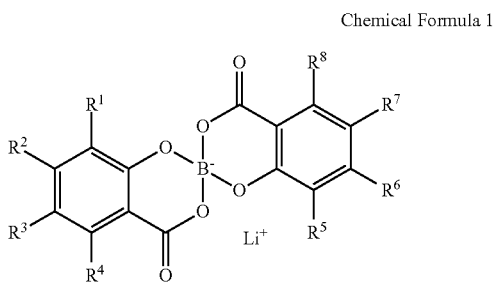

In Chemical Formula 1, $R^1$ to $R^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of $R^1$ to $R^8$ is a substituted or unsubstituted aryl group, a substituted or unsubstituted halogenated aryl group, or a combination thereof.

In the above Chemical Formula 1, at least one of $R^1$ to $R^8$ is a fluoroaryl group.

In the above Chemical Formula 1, at least one of $R^1$ to $R^8$ is 2,4-$F_2C_6H_3$.

The additive may be represented by the following Chemical Formula 1(a).

Chemical Formula 1(a)

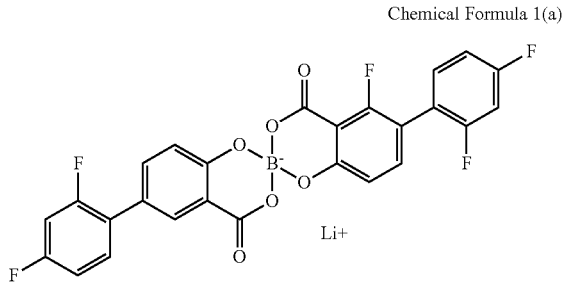 [SMILES: O=C1O[B-]2(OC(=O)c3c(ccc(-c4ccc(F)cc4F)c3F)O2)Oc2ccc(-c3ccc(F)cc3F)cc21 ; [Li+]]

The additive may be included in an amount of about 0.001 wt % to about 10 wt % based on the total weight of the electrolyte.

The electrolyte may further include an additive selected from lithium bis(oxalate)borate (LiBOB), lithium bis(salicylato)borate (LiBSB), and combinations thereof.

In yet another embodiment, a rechargeable lithium battery is provided that includes a positive electrode including a positive active material, a negative electrode including a negative active material, and the electrolyte.

The electrolyte may have high dissolution capability in a non-aqueous organic solvent and high affinity for the surface of a negative electrode while promoting formation of a passivation film on the surface of a positive electrode and/or a negative electrode. Accordingly, the electrolyte may improve cycle life and thermal stability of a rechargeable lithium battery.

DETAILED DESCRIPTION OF THE INVENTION

Figure 1:
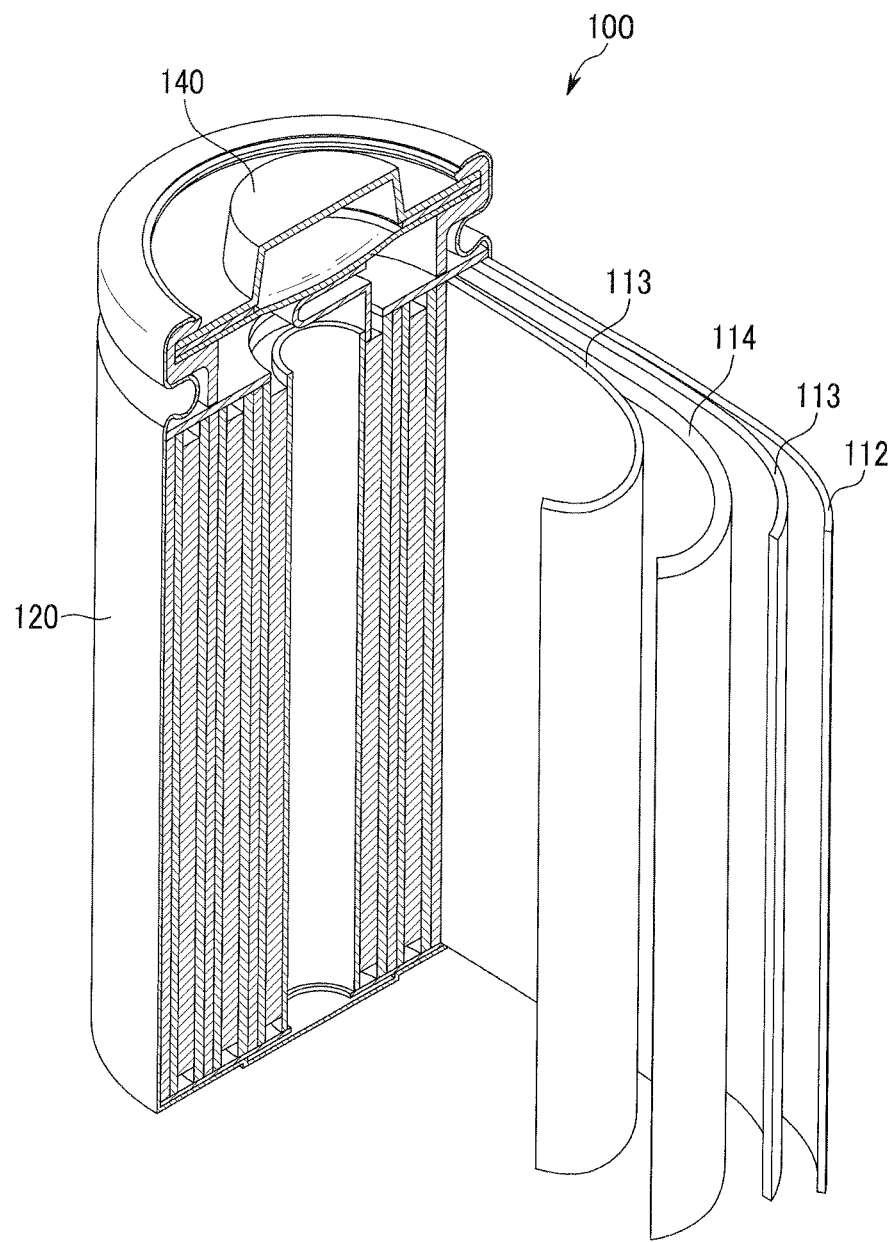
FIG. 1 is a schematic view showing a rechargeable lithium battery according to one embodiment.

This disclosure will be described more fully hereinafter, in which exemplary embodiments of the invention are shown. As those skilled in the art would realize, the described embodiments may be modified in various different ways, all without departing from the spirit or scope of the present invention.

As used herein, when a definition is not otherwise provided, the term "substituted" may refer to a substitutent selected from a halogen atom (F, Br, Cl, or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and combinations thereof.

As used herein, when a definition is not otherwise provided, the term "hetero" may refer to one including 1 to 3 heteroatoms selected from N, O, S, and P.

According to one embodiment, an electrolyte additive represented by the following Chemical Formula 1 is provided.

Chemical Formula 1

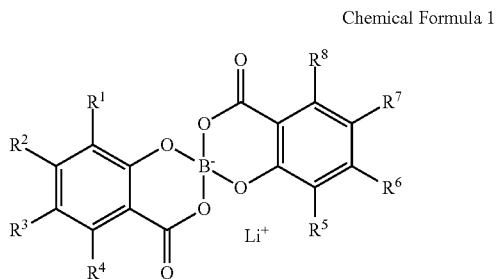

In Chemical Formula 1, $R^1$ to $R^8$ are each independently hydrogen, a substituted or unsubstituted C1 to C30 alkyl group, a substituted or unsubstituted. C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of $R^1$ to $R^8$ is a substituted or unsubstituted aryl group, a substituted or unsubstituted halogenated aryl group, or a combination thereof.

The compound represented by the above Chemical Formula 1 is a type of aryl or haloaryl substituted salicyclic organoborate. When added to an electrolyte, the compound may improve electrochemical characteristics and dissolution capability.

In the above Chemical Formula 1, at least one of $R^1$ to $R^8$ may be a fluoroaryl group and the fluoroaryl group may be, for example, $2,4\text{-}F_2C_6H_3$. For example, in Chemical Formula 1, $R^3$ and $R^7$ are $2,4\text{-}F_2C_6H_3$, and $R^1$, $R^2$, $R^4$, $R^5$, $R^6$, and $R^8$ are hydrogen. Herein, the compound represented by the above Chemical Formula 1 may be lithium bis[5-(2,4-difluorophenyl)salicylato-2-]borate represented by the following Chemical Formula 1(a).

Chemical Formula 1(a)

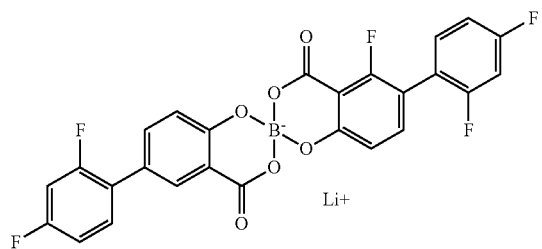

According to another embodiment, an electrolyte for a rechargeable lithium battery includes an additive represented by the following Chemical Formula 1, a non-aqueous organic solvent, and a lithium salt.

Chemical Formula 1

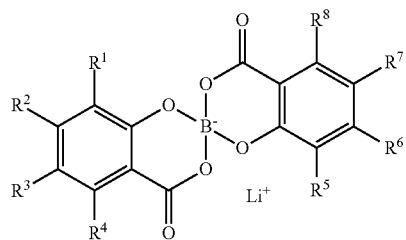

In Chemical Formula 1, $R^1$ to $R^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of $R^1$ to $R^8$ is a substituted or unsubstituted aryl group, a substituted or unsubstituted halogenated aryl group, or a combination thereof. For example, at least one of $R^1$ to $R^8$ may be a fluoroaryl group, and at least one of $R^1$ to $R^8$ may be $2,4\text{-}F_2C_6H_3$.

The additive may be a compound represented by the following Chemical Formula 1(a).

Chemical Formula 1(a)

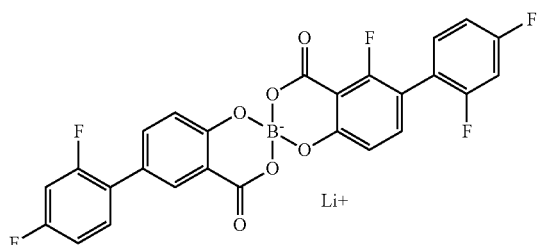

The additive represented by the above Chemical Formula 1 is a type of aryl or haloaryl substituted salicyclic organoborate. When added to an electrolyte, the additive may improve electrochemical characteristics and dissolution capability.

In particular, the additive represented by the above Chemical Formula 1 is reduced during the charge and discharge of a battery and may promote formation of a passivation film called a solid electrolyte interface (SEI) on the surface of a positive electrode and/or a negative electrode.

In addition, the additive represented by the above Chemical Formula 1 has high dissolution capability in a non-aqueous organic solvent described hereinafter and high affinity for a negative electrode.

In addition, the additive represented by the above Chemical Formula 1 may improve thermal stability and flame retardancy.

The additive may be included in an amount of about 0.001 wt % to about 10 wt % based on the total weight of the electrolyte. When the additive is included within this range, it may improve dissolution capability in an electrolyte while realizing the aforementioned effects.

The non-aqueous organic solvent plays a role of transmitting ions taking part in the electrochemical reaction of a battery.

The non-aqueous organic solvent may include a carbonate-based, ester-based, ether-based, ketone-based, alcohol-based, or aprotic solvent. The carbonate-based solvent may include dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), and the like, and the ester-based solvent may include methyl acetate, ethyl acetate, n-propyl acetate, dimethylacetate, methylpropionate, ethylpropionate, gamma-butyrolactone, decanolide, gamma-valerolactone, mevalonolactone, caprolactone, and the like. The ether-based solvent may include dibutyl ether, tetraglyme, diglyme, dimethoxyethane, 2-methyltetrahydrofuran, tetrahydrofuran and the like, and the ketone-based solvent may include cyclohexanone and the like. The alcohol-based solvent may include ethanol, isopropyl alcohol, and the like. The aprotic solvent includes nitriles such as R—CN (wherein R is a C2 to C20 linear, branched, or cyclic hydrocarbon group, and may include a double bond, an aromatic ring, or an ether bond), amides such as dimethylformamide, dimethylacetamide, dioxolanes such as 1,3-dioxolane, sulfolanes, and the like.

The non-aqueous organic solvent may be used singularly or in a mixture. When the organic solvent is used in a mixture, its mixture ratio can be controlled in accordance with desirable performance of a battery.

The carbonate-based solvent may include a mixture of a cyclic carbonate and a linear carbonate. The cyclic carbonate and the linear carbonate are mixed together in a volume ratio of about 1:1 to about 1:9, which may enhance performance of an electrolyte.

In addition, the non-aqueous organic solvent may be prepared by further adding the aromatic hydrocarbon-based solvent to the carbonate-based solvent. The carbonate-based solvent and the aromatic hydrocarbon-based solvent are mixed together in a volume ratio of about 1:1 to about 30:1.

The aromatic hydrocarbon-based organic solvent may be selected from the group consisting of benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and combinations thereof.

The lithium salt is dissolved in the non-aqueous organic solvent and supplies lithium ions in a rechargeable lithium battery, and basically operates the rechargeable lithium battery and improves lithium ion transfer between positive and negative electrodes. Such a lithium salt includes one or more of $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein, x and y are natural numbers), LiCl, and LiI.

The lithium salt may be used at a concentration of about 0.1 to about 2.0M. When the lithium salt is included within the above concentration range, it may improve electrolyte performance and lithium ion mobility due to optimal electrolyte conductivity and viscosity.

The electrolyte may further include an additive selected from lithium bis(oxalate)borate (LiBOB), lithium bis(salicylato)borate (LiBSB), and a combination thereof. The lithium bis(oxalate)borate (LiBOB) and/or lithium bis(salicylato)borate (LiBSB) improves thermal stability of an electrolyte and cycle life of a battery.

Hereinafter, a rechargeable lithium battery according to another embodiment is described referring to FIG. 1.

FIG. 1 is a schematic view of a rechargeable lithium battery according to one embodiment.

Referring to FIG. 1, a rechargeable lithium battery 100 according to one embodiment includes an electrode element including a positive electrode 114, a negative electrode 112 facing the positive electrode 114, a separator 113 interposed between the positive electrode 114 and negative electrode 112, and an electrolyte (not shown) impregnating the positive electrode 114, negative electrode 112, and separator 113, a battery case 120 including the electrode element, and a sealing member 140 sealing the battery case 120.

The positive electrode 114 includes a current collector and a positive active material layer disposed on at least one side of the current collector.

The current collector may be an aluminum (Al) foil, but is not limited thereto.

The positive active material layer includes a positive active material, a binder, and a conductive material.

The positive active material includes lithiated intercalation compounds that reversibly intercalate and deintercalate lithium ions. The positive active material may include a composite oxide including at least one selected from the compounds represented by the following chemical formulae:

$Li_aA_{1-b}X_bD_2$ ($0.90 \leq a \leq 1.8$, $0 \leq b \leq 0.5$); $Li_aA_{1-b}X_bO_{2-c}D_c$ ($0.90 \leq a \leq 1.8$, $0 \leq b \leq 0.5$, $0 \leq c \leq 0.05$); $Li_aE_{1-b}X_bO_{2-c}D_c$ ($0.90 \leq a \leq 1.8$, $0 \leq b \leq 0.5$, $0 \leq c \leq 0.05$); $Li_aE_{2-b}X_bO_{4-c}D_c$ ($0.90 \leq a \leq 1.8$, $0 \leq b \leq 0.5$, $0 \leq c \leq 0.05$); $Li_aNi_{1-b-c}Co_bX_cD_\alpha$ ($0.90 \leq a \leq 1.8$, $0 \leq b \leq 0.5$, $0 \leq c \leq 0.5$, $0 < \alpha \leq 2$); $Li_aNi_{1-b-c}Co_bX_cO_{2-\alpha}T_\alpha$ ($0.90 \leq a \leq 1.8$, $0 \leq b \leq 0.5$, $0 \leq c \leq 0.05$, $0 < \alpha < 2$); $Li_aNi_{1-b-c}Co_bX_cO_{2-\alpha}T_2$ ($0.90 \leq a \leq 1.8$, $0 \leq b \leq 0.5$, $0 \leq c \leq 0.05$, $0 < \alpha < 2$); $Li_aNi_{1-b-c}Mn_bX_cD_\alpha$ ($0.90 \leq a \leq 1.8$, $0 \leq b \leq 0.5$, $0 \leq c \leq 0.05$, $0 < \alpha \leq 2$); $Li_aNi_{1-b-c}Mn_bX_cO_{2-\alpha}T_\alpha$ ($0.90 \leq a \leq 1.8$, $0 \leq b \leq 0.5$, $0 \leq c \leq 0.05$, $0 < \alpha < 2$); $Li_aNi_{1-b-c}Mn_bX_cO_{2-\alpha}T_2$ ($0.90 \leq a \leq 1.8$, $0 \leq b \leq 0.5$, $0 \leq c \leq 0.05$, $0 < \alpha < 2$); $Li_aNi_bE_cG_dO_2$ ($0.90 \leq a \leq 1.8$, $0 \leq b \leq 0.9$, $0 \leq c \leq 0.5$, $0.001 \leq d \leq 0.1$); $Li_aNi_bCo_cMn_dG_eO_2$ ($0.90 \leq a \leq 1.8$, $0 \leq b \leq 0.9$, $0 \leq c \leq 0.5$, $0 \leq d \leq 0.5$, $0.001 \leq e \leq 0.1$); $Li_aNiG_bO_2$ ($0.90 \leq a \leq 1.8$, $0.001 \leq b \leq 0.1$); $Li_aCoG_bO_2$ ($0.90 \leq a \leq 1.8$, $0.001 \leq b \leq 0.1$); $Li_aMn_{1-b}G_bO_2$ ($0.90 \leq a \leq 1.8$, $0.001 \leq b \leq 0.1$); $Li_aMn_2G_bO_4$ ($0.90 \leq a \leq 1.8$, $0.001 \leq b \leq 0.1$); $Li_aMn_{1-g}G_gPO_4$ ($0.90 \leq a \leq 1.8$, $0 \leq g \leq 0.5$); $QO_2$; $QS_2$; $LiQS_2$; $V_2O_5$; $LiV_2O_5$; $LiZO_2$; $LiNiVO_4$; $Li_{(3-f)}J_2(PO_4)_3$ ($0 \leq f \leq 2$); $Li_{(3-f)}Fe_2(PO_4)_3$ ($0 \leq f \leq 2$); and $Li_aFePO_4$ ($0.90 \leq a \leq 1.8$).

In the above chemical formulae, A is selected from the group consisting of Ni, Co, Mn, and a combination thereof; X is selected from the group consisting of Al, Ni, Co, Mn, Cr, Fe, Mg, Sr, V, a rare earth element, and a combination thereof; D is selected from the group consisting of O, F, S, P, and a combination thereof; E is selected from the group consisting of Co, Mn, and a combination thereof; T is selected from the group consisting of F, S, P, and a combination thereof; G is selected from the group consisting of Al, Cr, Mn, Fe, Mg, La, Ce, Sr, V, and a combination thereof; Q is selected from the group consisting of Ti, Mo, Mn, and a combination thereof; Z is selected from the group consisting of Cr, V, Fe, Sc, Y, and a combination thereof; and J is selected from the group consisting of V, Cr, Mn, Co, Ni, Cu, and a combination thereof.

The foregoing compounds may have a coating layer on the surface, or may be mixed with another compound having a coating layer. The coating layer may include at least one coating element compound selected from the group consisting of an oxide of a coating element, a hydroxide of a coating element, an oxyhydroxide of a coating element, an oxycarbonate of a coating element, and a hydroxylcarbonate of a coating element. The compound for the coating layer may be amorphous or crystalline. The coating element included in the coating layer may include Mg, Al, Co, K, Na, Ca, Si, Ti, V, Sn, Ge, Ga, B, As, Zr, or a mixture thereof. The coating layer may be disposed in a method having no adverse influence on properties of a positive active material by using these elements in the compound. For example, the method may include any coating method such as spray coating, dipping, and the like, but is not illustrated in more detail since it is well-known to those who work in the related field.

The positive active material may be included in an amount of about 90 wt % to about 98 wt % based on the total amount of the positive active material layer.

The binder improves properties of binding positive active material particles among one another and, also, the positive active material with a current collector. Examples of the binder include polyvinyl alcohol, carboxylmethyl cellulose, hydroxypropyl cellulose, diacetyl cellulose, polyvinyl chloride, carboxylated polyvinyl chloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but are not limited thereto.

The conductive material is included to endow conductivity to an electrode. It may include any electrically conductive material, unless it causes a chemical change. Examples of the conductive material include a carbon-based material such as natural graphite, artificial graphite, carbon black, acetylene black, ketjen black, carbon fiber, and the like; a metal-based material such as a metal powder, a metal fiber, or the like that includes copper, nickel, aluminum, silver, and the like; a conductive polymer such as a polyphenylene derivative; or a mixture thereof.

The binder and conductive material may each independently be included in an amount of about 1 wt % to 5 wt % based on the total amount of the positive active material layer.

The positive electrode 114 may be fabricated by mixing the positive active material, the binder, and the conductive material in a solvent to prepare a positive active material slurry, and coating the positive active material slurry on a current collector. The solvent includes N-methylpyrrolidone or the like, but is not limited thereto. The electrode-fabricating method is well known and thus is not described in detail in the present specification.

The negative electrode 112 may include a current collector and a negative active material layer disposed on at least one side of the current collector.

The current collector may include a copper foil, a nickel foil, a stainless steel foil, a titanium foil, a nickel foam, a copper foam, a polymer substrate coated with a conductive metal, or a combination thereof.

The negative active material layer may include a material that reversibly intercalates/deintercalates lithium ions, a lithium metal, a lithium metal alloy, a material capable of doping and dedoping lithium, or a transition metal oxide.

The material that reversibly intercalates/deintercalates lithium ions includes a carbon material. The carbon material may be any generally-used carbon-based negative active material in a lithium ion rechargeable battery. Examples of the carbon material include crystalline carbon, amorphous carbon, and mixtures thereof. The crystalline carbon may be non-shaped or sheet-, flake-, spherical-, or fiber-shaped natural graphite or artificial graphite. The amorphous carbon may be a soft carbon, a hard carbon, mesophase pitch carbonization products, fired coke, and the like.

Examples of the lithium metal alloy include lithium and a metal of Na, K, Rb, Cs, Fr, Be, Mg, Ca, Sr, Si, Sb, Pb, In, Zn, Ba, Ra, Ge, Al, or Sn.

The material capable of doping and dedoping lithium may include Si, SiO$_x$ (0<x<2), a Si—C composite, a Si-Q alloy (wherein Q is an alkali metal, an alkaline-earth metal, an element of one of Groups 13 to 16, a transition element, a rare earth element, or a combination thereof, and is not Si), Sn, SnO$_2$, a Sn—C composite, a Sn—R alloy (wherein R is an alkali metal, an alkaline-earth metal, an element of one of Groups 13 to 16, a transition element, a rare earth element, or a combination thereof, and is not Sn), and the like. At least one of these materials may be mixed with SiO$_2$. The elements Q and R may include an element selected from Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, or a combination thereof.

The transition metal oxide may include vanadium oxide, lithium vanadium oxide, and the like.

The binder improves properties of binding active material particles with one another and a negative active material with a current collector. The binder may include a non-water-soluble binder, a water-soluble binder, or a combination thereof.

The non-water-soluble binder may include polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, or a combination thereof.

The water-soluble binder may include a styrene-butadiene rubber, an acrylated styrene-butadiene rubber, a polyvinylalcohol, sodium polyacrylate, a copolymer of propylene and C2 to C8 olefin, a copolymer of (meth)acrylic acid and (meth)acrylic acid alkylester, or a combination thereof.

When the water-soluble binder is used as a negative electrode binder, a cellulose-based compound may be further used to improve viscosity. As for the cellulose-based compound, at least one kind of carboxylmethyl cellulose, hydroxypropylmethyl cellulose, methyl cellulose, and alkali metal salts thereof may be mixed and used. The alkaline metal may be Na, K, or Li. The cellulose-based compound may be included in an amount of 0.1 to 3 parts by weight based on 100 parts by weight of the negative active material.

The conductive material is included to improve electrode conductivity. Any electrically conductive material may be used as a conductive material unless it causes a chemical change. Examples of the conductive material include: a carbon-based material such as natural graphite, artificial graphite, carbon black, acetylene black, ketjen black, carbon fiber, and the like; a metal-based material including a metal powder or a metal fiber including copper, nickel, aluminum, silver, and the like; a conductive polymer such as polyphenylene derivative, and the like; or a mixture thereof.

The negative electrode may be fabricated by mixing the negative active material, binder and optionally conductive agent in a solvent to prepare a negative active material slurry, and coating the negative active material slurry on a current collector followed by drying and compressing. The solvent includes N-methylpyrrolidone and the like, but is not limited thereto. The electrode fabricating method is well known, and thus is not described in detail in the present specification.

The separator 113 separates the positive electrode 114 and negative electrode 112 and provides a path for transferring lithium ions. The separator 113 may be any separator that is generally used in a lithium ion battery. In other words, the separator may have low resistance against electrolyte ions and excellent moisturizing capability of an electrolyte. For example, the separator may be selected from a glass fiber, polyester, TEFLON (tetrafluoroethylene), polyethylene, polypropylene, polytetrafluoroethylene (PTFE), or a combination thereof and may be a non-woven fabric type or a fabric type. For example, a polyolefin-based polymer separator such as polyethylene, polypropylene, and the like is used for a lithium ion battery, and a separator coated with a ceramic component or a polymer material may be used to improve heat resistance or mechanical strength. The separator may have a singular layer or multiple layers.

The rechargeable lithium battery may be classified as a lithium ion battery, a lithium ion polymer battery, or a lithium polymer battery according to the presence of a separator and the kind of electrolyte used therein. The rechargeable lithium battery may have a variety of shapes and sizes, and thus may include a cylindrical-, prismatic-, coin-, or pouch-type battery and be the size of a thin film type or a bulky type battery. The structure and fabricating method for a lithium ion battery pertaining to the present invention are well known in the art.

The electrolyte is as described above.

The following examples illustrate the present invention in more detail. These examples, however, should not in any sense be interpreted as limiting the scope of the present invention.

Synthesis Example 1

Preparation of Additive 2.5020 g (0.01 mol) of 5-(2,4-difluorophenyl)salicylic acid, 0.2098 g (0.005 mol) of lithium hydroxide monohydrate, and 0.3092 g (0.005 mol) of boric acid were put in a flask, and an acetonitrile/methanol (2/1, v/v) solvent was added thereto, preparing a mixed solution. The mixed solution was refluxed for 8 hours and agitated at room temperature for one night. Next, the solution was concentrated down to ¼ thereof and allowed to stand at room temperature, obtaining a white crystal. The white crystal was filtrated and recrystallized using an acetonitrile/methanol solvent. Then, the recrystallized product was dried in a 100° C. vacuum oven for 24 hours, obtaining the following lithium bis[5-(2,4-difluorophenyl)salicylato-2-]borate (LiBDB). The LiBDB may also be called lithium bis(2',4'-difluoro-4-hydroxybiphenyl-3-carboxylato)borate (LiBDB).

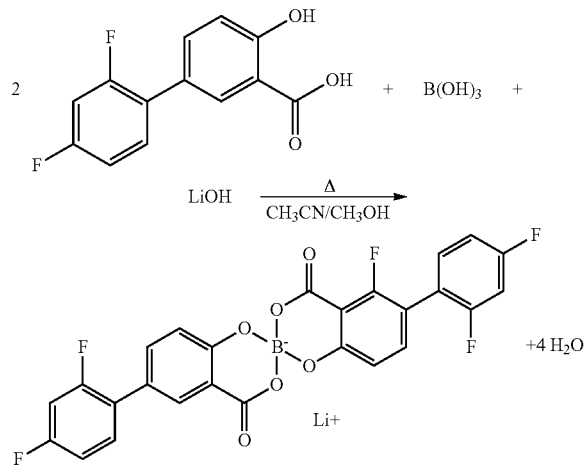

The compound has an NMR spectrum as follows:
$^{11}$B NMR (128.27 MHz, Methanol-d4): 2.67 ppm.

Thermal Analysis of Additive

The LiBDB according to Synthesis Example 1 was heated under a nitrogen atmosphere at an increasing rate of 10° C./min and subjected to thermogravimetric analysis (TGA).

Figure 2:
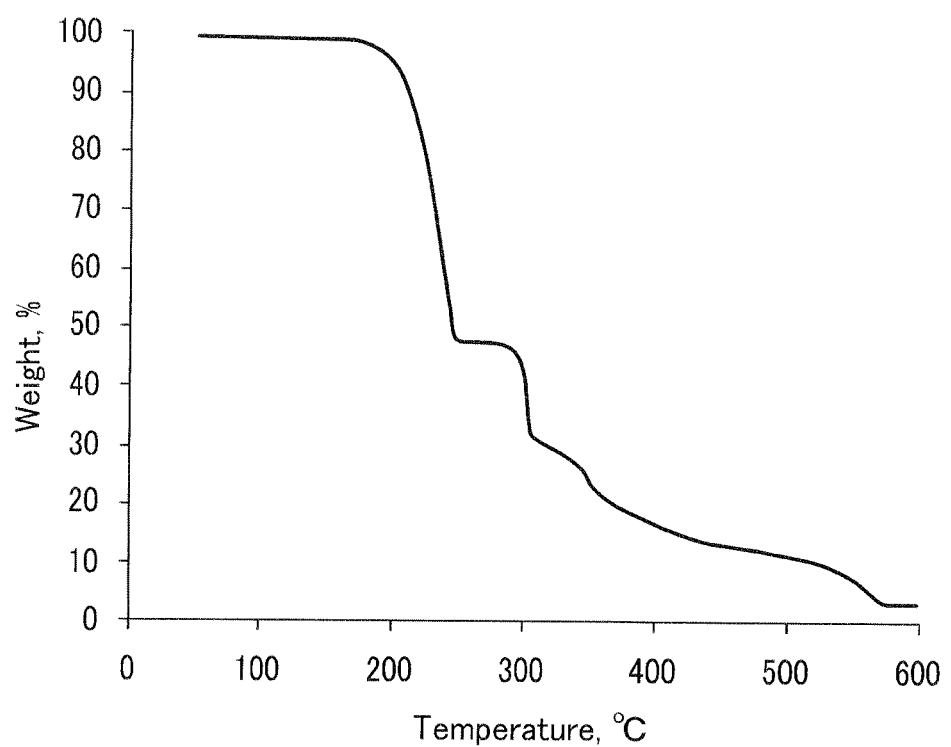
FIG. 2 is a thermogravimetric analysis (TGA) graph showing the lithium bis[5-(2,4-difluorophenyl)salicylato-(2-)]borate according to Synthesis Example 1.

FIG. 2 shows the thermogravimetric analysis (TGA) graph of the LiBDB according to Synthesis Example 1.

Referring to FIG. 2, the LiBDB had a decomposition peak at about 210° C. and thus, better thermal stability than LiPF$_6$, which has a decomposition peak at about 70° C.

Example 1

Preparation of Electrolyte

A 1M LiPF$_6$ lithium salt was added to a mixed solvent prepared by mixing ethylene carbonate (EC), ethylmethyl carbonate (EMC), and dimethyl carbonate (DMC) in a volume ratio of 3/4/3 (v/v/v), and 0.1 wt % of the LiBDB according to Synthesis Example 1 was added to the mixture, making an electrolyte for a rechargeable lithium battery.

Example 2

An electrolyte for a rechargeable lithium battery was prepared according to the same method as Example 1, except that 0.5 wt % of the LiBDB according to Synthesis Example 1 was used instead of 0.1 wt %.

Comparative Example 1

An electrolyte for a rechargeable lithium battery was prepared according to the same method as Example 1, except that 0.1 wt % of the LiBDB according to Synthesis Example 1 was not used.

Comparative Example 2

An electrolyte for a rechargeable lithium battery was prepared according to the same method as Example 2, except that 0.5 wt % of lithium bis(oxalate)borate (LiBOB) was used instead of 0.5 wt % of the LiBDB according to Synthesis Example 1.

Evaluation 1: Capacity Retention

Rechargeable lithium batteries were fabricated using each respective electrolyte according to Examples 1 and 2 and Comparative Examples 1 and 2. Herein, a positive electrode was fabricated using a positive active material including LiMn$_2$O$_4$ and LiNi$_{0.3}$Co$_{0.3}$Mn$_{0.3}$O$_2$ in a weight ratio of 2:8. The negative electrode used a negative active material including artificial graphite.

The rechargeable lithium batteries including the respective electrolytes according to Examples 1 and 2 and Comparative Example 1 were charged and discharged 100 times with 1 C at 25° C. and measured regarding discharge capacity at each cycle.

Figure 3:
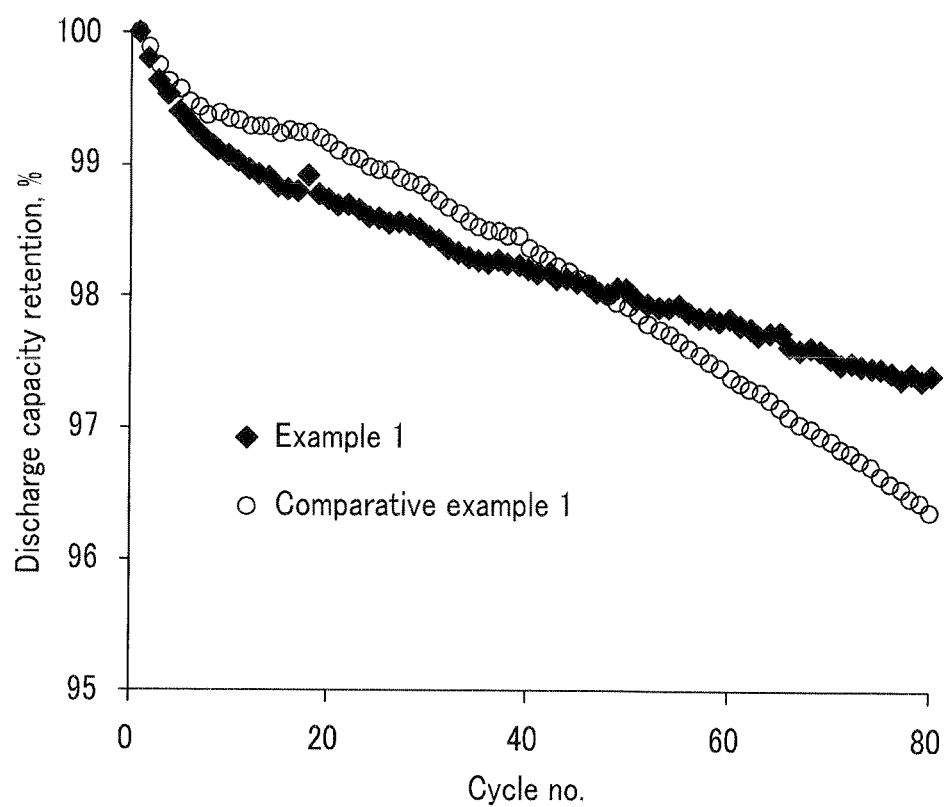
FIG. 3 is a graph showing discharge capacity of rechargeable lithium battery cells respectively including the electrolytes according to Example 1 and Comparative Example 1 as a function of number of cycles.

FIG. 3 is a graph showing discharge capacity of the rechargeable lithium batteries including the electrolytes according to Example 1 and Comparative Example 1 as a function of number of cycles.

Referring to FIG. 3, the rechargeable lithium batteries including the electrolyte according to Example 1 had higher discharge capacity retention after 50 cycles than the rechargeable lithium battery including the electrolyte according to Comparative Example 1.

Evaluation 2: Differential Capacity

Half-cells were fabricated using the respective electrolytes according to Example 2 and Comparative Examples 1 and 2. Herein, a positive electrode using a positive active material was prepared by mixing LiMn$_2$O$_4$ and LiNi$_{0.3}$Co$_{0.3}$Mn$_{0.3}$O$_2$ in a weight ratio of 2:8, while its counter electrode used a lithium metal.

The half-cell was charged and discharged once with 0.2 C and measured regarding differential capacity (dQ/dV).

Figure 4:
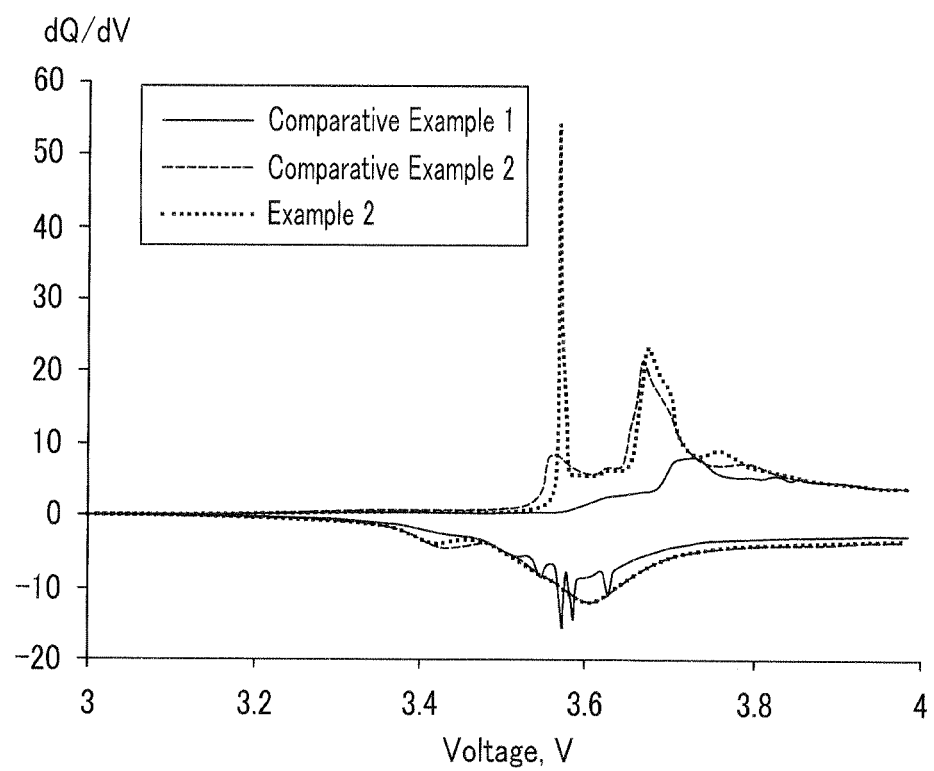
FIG. 4 is a graph showing differential capacity (dQ/dV) of half-cells respectively including the electrolytes according to Examples 1 and 2 and Comparative Example 1 as a function of voltage.

FIG. 4 is a graph showing differential capacity (dQ/dV) of the half-cells including the electrolytes according to Example 2 and Comparative Examples 1 and 2 as a function of voltage.

Referring to FIG. 4, the half-cell including the electrolyte according to Example 2 had a peak at about 3.58 V, which was caused by the decomposition of the LiBDB. On the other hand, the half-cells including the respective electrolytes according to Comparative Examples 1 and 2 had no peak at 3.58 V.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An electrolyte additive comprising a compound represented by the following Chemical Formula 1:

Chemical Formula 1

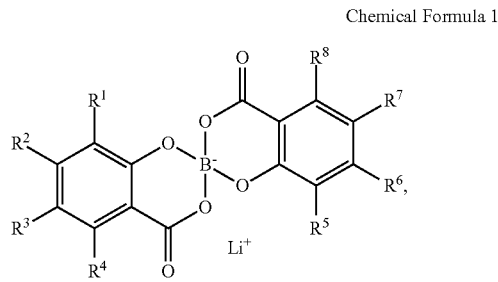

wherein

R$^1$ to R$^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C26 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of R$^1$ to R$^8$ is a fluoroaryl group.

2. The electrolyte additive of claim 1, wherein at least one of R$^1$ to R$^8$ is 2,4-F$_2$C$_6$H$_3$.

3. The electrolyte additive of claim 1, wherein the compound represented by Chemical Formula 1 is a compound represented by the following Chemical Formula 1(a):

Chemical Formula 1(a)

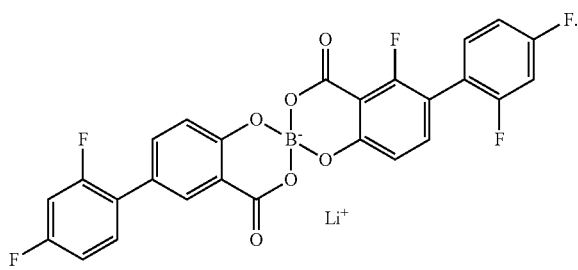

4. An electrolyte for a rechargeable lithium battery, comprising
an additive represented by the following Chemical Formula 1,
a non-aqueous organic solvent, and
an electrolyte including a lithium salt:

Chemical Formula 1

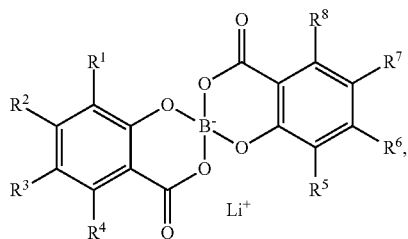

wherein

R$^1$ to R$^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of R$^1$ to R$^8$ is a fluoroaryl group.

5. The electrolyte for a rechargeable lithium battery of claim 4, wherein at least one of R$^1$ to R$^8$ of Chemical Formula 1 is 2,4-F$_2$C$_6$H$_3$.

6. The electrolyte for a rechargeable lithium battery of claim 4, wherein the electrolyte additive represented by Chemical Formula 1 is an electrolyte additive represented by the following Chemical Formula 1(a):

Chemical Formula 1(a)

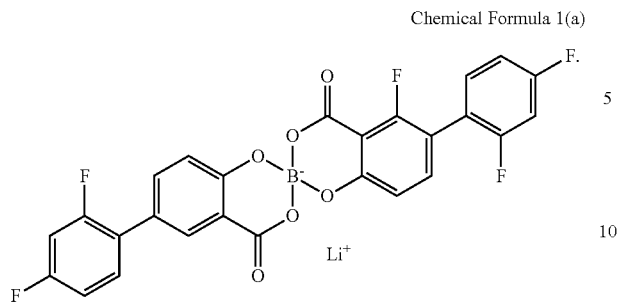

Chemical Formula 1

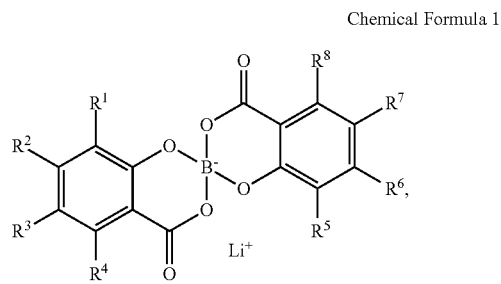

wherein
$R^1$ to $R^8$ are each independently hydrogen, a substituted or unsubstituted C1 to C30 alkyl group, a substituted or unsubstituted C3 to C30 cycloalkyl group, C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 an arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, a substituted or unsubstituted C1 to C20 aldehyde group, a substituted or unsubstituted amino group, a halogen, a cyano group, a nitric acid group, or a combination thereof, and at least one of $R^1$ to $R^8$ is a fluoroaryl group.

7. The electrolyte for a rechargeable lithium battery of claim 4, wherein the additive is included in an amount of about 0.001 wt % to about 10 wt % based on the total weight of the electrolyte.

8. The electrolyte for a rechargeable lithium battery of claim 4, wherein the electrolyte further comprises an additive selected from lithium bis(oxalate)borate (LiBOB), lithium bis(salicylato)borate (LiBSB), or a combination thereof.

9. A rechargeable lithium battery, comprising:

a positive electrode including a positive active material, a negative electrode including a negative active material, and an electrolyte comprising an additive represented by the following Chemical Formula 1, a non-aqueous organic solvent, and an electrolyte including a lithium salt:

\* \* \* \* \*